United States Patent [19]

Trandai et al.

[11] Patent Number: 5,605,681
[45] Date of Patent: Feb. 25, 1997

[54] MILD GEL DEODORANT COMPOSITION CONTAINING SOAP, POLYMERIC HYDROGEL FORMING POLYMER AND HIGH LEVEL OF WATER

[75] Inventors: Angie Trandai; Dean Van Phan, both of West Chester, Ohio

[73] Assignee: The Proctor & Gamble Company, Cincinnati, Ohio

[21] Appl. No.: 307,951

[22] Filed: Sep. 16, 1994

[51] Int. Cl.$^6$ .................................................. A61K 7/32
[52] U.S. Cl. ................................................................ 424/65
[58] Field of Search ................................................ 424/65

[56] References Cited

U.S. PATENT DOCUMENTS

| | | | |
|---|---|---|---|
| 4,822,602 | 4/1989 | Sabatelli | 424/65 |
| 4,970,220 | 11/1990 | Chaussee | 514/358 |
| 5,114,717 | 5/1992 | Kuznitz | 424/401 |
| 5,385,729 | 1/1995 | Prencipe | 424/70.11 |

*Primary Examiner*—C. Warren Ivy
*Assistant Examiner*—Evelyn Huang
*Attorney, Agent, or Firm*—Tara M. Rosnell; Leonard W. Lewis

[57] ABSTRACT

Provided is a deodorant gel composition having improved mildness to the skin through the use of increased level of water and polyethylene glycol solvent, such composition comprising (a) from about 0.001% to about 20%, by weight, of deodorant active, fragrance, or a combination thereof; (b) from about 0.1% to about 15%, by weight, of a soap gelling agent selected from the group consisting of salts of $C_{12}$–$C_{40}$ fatty acids, and combinations thereof; (c) a hydrogel component comprising from about 0.001% to about 5%, by weight of the composition, of hydrogel forming crosslinked polymeric gelling agent, said hydrogel forming polymeric gelling agent being incorporated in said composition as a gel; (d) from about 5% to about 70%, by weight, of a polyhydroxy solvent for said soap gelling agent, said polyhydroxy solvent being selected from the group consisting of: alkyl alcohols having at least three hydroxy groups; polymers of $C_3$–$C_{12}$ alcohols having at least three hydroxy groups per monomer wherein the polymers have a weight average molecular weight of about 800 or less; polyoxyethylenes, polyoxypropylenes, and polyoxyethylene/polyoxypropylene copolymers, having a weight average molecular weight of from about 200 to about 4,000; copolymers of $C_3$–$C_{12}$ alcohols having at least three hydroxy groups with $C_2$–$C_{10}$ dihydric alcohols, said copolymers having a weight average molecular weight of from about 200 to about 4,000; and combinations thereof; and (e) at least about 25%, by weight, water.

22 Claims, No Drawings

MILD GEL DEODORANT COMPOSITION CONTAINING SOAP, POLYMERIC HYDROGEL FORMING POLYMER AND HIGH LEVEL OF WATER

FIELD OF INVENTION

This invention relates to gel deodorant compositions containing hydrogel forming polymeric gelling agent and water

BACKGROUND OF THE INVENTION

Human body malodors are generally believed to be caused in part 5 by microbial interaction with sweat gland secretions which produces pungent fatty acids. Aside from cleansing, one way such odors are controlled is by the use of deodorant products, particularly in the underarm area of the body.

Deodorant products generally contain a safe and effective level of perfume or other odor masking ingredients, an antimicrobial active ingredient, or a combination thereof, incorporated into a vehicle from which the active ingredients may be deposited on the skin. The deodorant products of the present invention relate to gel deodorant compositions. These gel products may be in the form of solid sticks, semi-solid sticks, or other softer, gel products.

Gel deodorant compositions have several advantages over other types of stick formulations. For example, they usually leave no more than a minimal amount of residue on the skin, and they glide easily over the skin when applied. Deodorant compositions of the gel type generally incorporate three key ingredients: a material known to have deodorant efficacy, a gelling agent, and a polar solvent system.

The gelling agents used most often in deodorant gel compositions are of the fatty acid soap type. The gelling agents used in these compositions include, for instance, the sodium or potassium salts of $C_{12}$–$C_{22}$ fatty acids. These types of gel compositions most often utilize a highly polar alcohol solvent as the primary polar solvent ingredient, which is necessary to form the gel structure with the gelling agent. Monohydric and dihydric alcohols, especially, propylene glycol and dipropylene glycol, are typically used for this purpose. The gel deodorant compositions of this type typically contain some water, however the amount of water is limited since its presence decreases solubility of the gelling agent and, consequently, can negatively affect structural integretity of the gel as well as impart a wet feel to the product.

Although alcohol/soap gel deodorants are quite popular and commonly used, it would be desirable to provide an improved alcohol/soap deodorant gel composition that exhibited improved mildness to the user. It is an object of the present invention to provide such a composition. It is also an object of the present invention to provide gel S deodorant compositions having reduced levels of polar solvents that can be relatively irritating to the skin, e.g., mono-and dihydric alcohols such as propylene glycol and dipropylene glycol, and to replace them with milder ingredients.

It is another object of this invention to provide gel deodorant compositions containing decreased levels of mono- and di-hydric alcohols for reduced skin irritation and increased levels of water while retaining a similar overall level of gel integrity without causing excessive, undesirable wet feel on the skin. These and other benefits of the present invention as may be disclosed or become apparent to those skilled in the art can be obtained according to the invention described below.

All percentages herein are by weight of the compositions unless otherwise indicated. All ratios are weight ratios unless otherwise indicated. All percentages, ratios, and levels of ingredients referred to herein are based on the actual amount of the ingredient, and do not include solvents, fillers, or other materials with which the ingredient may be combined as commercially available products, unless otherwise indicated.

The invention hereof can comprise, consist of, or consist essentially of the essential elements described herein as well as any of the preferred or optional ingredients also described herein.

SUMMARY OF THE INVENTION

It has now been found that gel deodorant compositions with improved mildness and increased amounts of water can be obtained by incorporating into the product an aqueous gel prepared from a highly absorbent, polymeric gelling material and a relatively high amount of water. Lower levels of conventional soap-type gelling agents and consequently, reduced or zero levels of mono- and di-hydric alcohol polar solvents are required to form the soap-based gel. Consequently, mild polar solvents, e.g., polyhydric alcohols such as polyethylene glycol, can be used to solubilize the soap-type gelling agent. As a result of this invention, gel deodorant compositions having improved skin mildness but still retaining similar overall gel rheology can be provided.

In particular, this invention provides a gel deodorant composition comprising:

(a) from about 0.001% to about 50%, by weight, of deodorant active, fragrance, or combination thereof;

(b) from about 0.1% to about 15%, by weight, of a soap gelling agent selected from the group consisting of salts of $C_{12}$–$C_{40}$ fatty acids, and combinations thereof;

(c) a hydrogel component comprising from about 0.001% to about 5%, by weight of the composition, of hydrogel-forming crosslinked polymeric gelling agent, said hydrogel-forming polymeric gelling agent being present in said composition as a gel;

(d) from about 5% to about 70%, by weight, of polyhydroxy solvent for said soap gelling agent, said polyhydroxy solvent being selected from the group consisting of: $C_3$–$C_{12}$ alkyl alcohols having at least three hydroxy groups; polymers of $C_3$–$C_{12}$ alcohols having at least three hydroxy groups per monomer wherein the polymers have a weight average molecular weight of about 800 or less; polyoxyethylenes, polyoxypropylenes, and polyoxyethylene/polyoxypropylene copolymers, having a weight average molecular weight of from about 200 to about 4,000; and copolymers of $C_3$–$C_{12}$ alcohols having at least three hydroxy groups with $C_2$–$C_{10}$ dihydric alcohols, said copolymers having a weight average molecular weight of from about 200 to about 4,000; and combinations thereof; and (e) at least about 25%, by weight, water.

The present invention is described in more detail below.

DETAILED DESCRIPTION OF THE INVENTION

The essential ingredients as well as a variety of preferred and optional ingredients for the compositions of the present invention are described below.

Active Ingredients

The deodorant compositions hereof comprise from about 0.001% to about 50%, by weight, deodorant active, fragrance, or combination thereof, preferably from about 0.01% to about 20%, preferably from about 0.1% to about 10%. Higher or lower levels are also contemplated and intended to be encompassed as long as they are safe and effective for topical application to the skin to control malodor. For purposes hereof, a deodorant active shall be defined as an ingredient which prevents or eliminates malodors from perspiration, as opposed to a fragrance which covers or masks odors.

Deodorant Active Ingredients

Suitable types of deodorant actives include antimicrobial ingredients such as bactericides and fungicides. Exemplary deodorant actives include quaternary ammonium compounds such as cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichlorio-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Still other antimicrobial ingredients include farnesol.

Other deodorant actives include odor absorbing materials such as carbonate and bicarbonate salts, e.g. as the alkali metal carbonates and bicarbonates, ammonium and tetraalkylammonium carbonates and bicarbonates, especially the sodium and potassium salts.

Mixtures of deodorant actives are also contemplated and intended to be encompassed herein.

Fragrance

The compositions of the present invention can contain a fragrance, or perfume, to impart a desired aroma, or to mask odors that may be associated with other components of the compositions. In the present invention the fragrance is generally used at a level from about 0.01% to about 10%, preferably from about 0.05% to about 7%, more preferably from about 0.1% to about 4%.

Any fragrance suitable for application to the skin can be used herein including a wide variety of fragrances and perfumes that are known to those skilled in the art. The particular fragrance used is largely a matter of choice, however, the fragrance should be used at a level effective for providing a noticeable aroma to the composition, or for masking undesired aroma of the composition. Also, the fragrance and whatever carriers accompany it should not impart excessive stinging to the skin, especially broken or irritated skin, at the levels previously disclosed. The fragrance can be water soluble or water insoluble, however it generally will be soluble in the composition hereof, typically in either water or the polar solvent system.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308, Hooper et al., issued Mar. 30, 1982, and U.S. Pat. No. 4,304,679, Hooper et al., issued Dec. 8, 1981, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinold and opoponax resinold); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as Coumarin and B-naphthyl methyl ether); esters (such as diethyl phthalate, phenylethyl phenylacetate, non-anolide-1:4). Fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Fragrance used in the present invention may also contain solubilizers, diluents, or solvents which are well known in the art. Such materials are described in Arctander, Perfume and Flavour Chemicals (Aroma Chemicals), Vol. I and II (1969). These materials typically include dipropylene glycol, diethylene glycol, $C_1$–$C_6$ alcohols, and benzyl alcohol.

Soap Gelling Agent

The compositions hereof will comprise from about 0.1% to about 15%, by weight, of a soap gelling agent, preferably from about 0.5% to about 10%, more preferably from about 1% to about 5%.

The soap gelling agents hereof are salts of fatty acids containing from about 12 to about 40 carbon atoms ($C_{12}$–$C_{40}$), preferably salts of $C_{12}$–$C_{22}$ fatty acids, more preferably $C_{14}$–$C_{20}$, most preferably $C_{16}$–$C_{20}$. Suitable salt forming cations for use in these gelling agents include metal salts such as alkali metals, e.g. sodium and potassium, alkaline earth metals, e.g. magnesium, and aluminum. Preferred are sodium and potassium salts.

Examples of fatty acids useful in synthesizing the gel forming agents herein include myristic, palmitic, stearic, oleic, linoleic, linolenic, margaric and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids, and greases.

Preferred fatty acid soap type gel forming agents include sodium stearate, sodium palmitate, potassium stearate, potassium palmitate, sodium myristate, and aluminum monostearate. The most preferred gel forming agent is sodium stearate.

Mixtures of soap gelling agents can also be used.

Polyhydroxy Solvent

The compositions of the present invention will comprise from about 5%, to about 70%, by weight, of a polyhydroxy solvent for the soap gelling agent, preferably from about 10% to about 60%, more preferably from about 20% to about 50%, most preferably from about 25% to about 45%.

The polyhydroxy solvent hereof is selected from the group consisting of: $C_3$–$C_{12}$ alcohols having at least three hydroxy groups; polymers of $C_3$–$C_{12}$ alcohols having at least three hydroxy groups per monomer wherein the polymer has a weight average molecular weight of about 800 or less; polyoxyethylene polymers, polyoxypropylene polymers, and polyoxyethylene/polyoxypropylene copolymers, such ethoxylated and propoxylated polymers having a weight average molecular weight of from about 200 to about 4,000, preferably from about 200 to about 2,000, more preferably from about 200 to about 800, most preferably from about 200 to about 600; and combinations thereof. Still other polyhydroxy solvents for use herein include copolymers of the above referenced tri-hydroxy or higher substituted $C_3$–$C_{12}$ alcohols with $C_2$–$C_{10}$ dihydric alcohols, such as ethylene glycol and propylene glycol. As will be well understood by those skilled in the art, the weight average molecular weight of such copolymers can vary widely depending upon the proportions of tri-hydric (or higher hydroxy-substituted) monomer to di-hydric monomer. In general, the weight average molecular weight of these copolymers will be from about 200 to about 4,000, preferably from about 200 to about 800.

References herein to the above polyhydroxy solvents shall be understood to include derivatives as would be useful as solvents for the soap gelling agent. Suitable derivatives of the polyhydroxy solvents hereof are alkyl ether derivatives (preferably $C_1$–$C_{18}$, more preferably $C_1$–$C_{16}$, most preferably $C_1$–$C_4$). Exemplary alkyl ether derivatives include ethyl, propyl, and butyl ether derivatives. Examples of such compounds are the ethyl, propyl, and butyl ether derivatives of PEG, PPG, or PEG/PPG polypropylene/polyethylene glycol copolymers, such as PPG-5-buteth-7. Other derivatives can also be used as the polyhydroxy solvent for the soap gelling agent as long as the soap gelling agent is soluble in such material and a gel which is stable at typical ambient usage temperatures can be formed, in particular, 25° C.

As discussed above, $C_3$–$C_{12}$ hydroxy solvents with at least 3 hydroxy groups can also be used as the solvent for the soap gelling agent. Preferred are $C_3$–$C_{12}$ trihydric alcohols, such as the $C_3$–$C_{12}$ alkyl alcohols, more preferably $C_3$–$C_6$, most preferably $C_3$ (e.g., glycerol). Polymers of such trihydric or higher hydroxy-substituted solvents can also be used, such polymers generally having weight average molecular weights of about 800 or less.

Preferred polyhydroxy solvents include tri-hydroxy $C_3$–$C_{12}$ alkyl alcohols, e.g., glycerol, and polymers of $C_3$–$C_6$ tri-hydroxy alcohols, e.g., polyglycerol, polyethylene glycol (PEG) having an average degree of ethoxylation of at least about 4, polyethylene glycol (PEG)/polypropylene glycol (PPG) copolymers having an average degree of ethoxylation of at least about 3.

Especially preferred solvents for the soap gelling agent are glycol, polyglycerol, PEG's having an average degree of ethoxylation (n) of from about 4 to about 30, more preferably from about 4 to about 22, even more preferably from about 4 to about 14, most preferably from about 4 to about 10, and PEG/PPG copolymers having an average degree of ethoxylation of from about 3 to about 30, more preferably from about 4 to about 10, and an average degree of propoxylation (m) of from about 3 to about 30, more preferably from about 2 to about 10, and a ratio of (m)/(m+n) of about 0.5 or less, preferably about 0.3 or less, and alkyl ether derivatives thereof. Higher degrees of ethoxylation and/or propoxylation, as well as higher ratios of (m)/(m+n) can be used as long as a gel can be formed which is stable at ambient temperatures, e.g. 25° C.

Combinations of the above polyhydroxy solvents can also be used. Preferred combinations of solvents are glycerol and/or polyglycerol used in combination with PEG and/or PEG/PPG copolymers, at a weight ratio of from about 5:1 to about 1:5, more preferably from about 1:3 to about 3:1, most preferably from about 3:2 to about 2:3.

Other polar solvents may be used in the present compositions as optional ingredients. These include, for example, monohydric $C_2$–$C_{10}$ alkyl alcohols, dihydric $C_3$–$C_{12}$ alkyl alcohols, alkyl ethers thereof (preferably $C_1$–$C_4$ alkyl ethers), and mixtures thereof.

Examples of such optional solvents include diethylene glycol, triethylene glycol, hexylene glycol, dipropylene glycol, tripropylene glycol, ethanol, n-propanol, n-butanol, t-butanol, 2-methoxyethanol, 2-ethyoxyethanol, ethylene glycol, isopropanol, isobutanol, diethylene glycol monomethylether, diethylene glycol monoethylether, 1,2-propylene glycol, 1,3-propylene glycol, 1,4-butylene glycol, 1,2-butylene glycol, 1,3-butylene glycol, 2,3-butylene glycol, 2,4-dihydroxy-2-methylpentane, trimethylene glycol, glycerine, 1,3-butane diol, 1,4-butane diol, and the like, and mixtures thereof.

Monohydric alcohols used herein not only provide solvency, but also provide certain cosmetic advantages such as cool feel to the skin and a strong scent which confirms the deodorant's presence to the user. Preferred monohydric alcohols for such purpose include, for example, methanol, ethanol, isopropanol, and mixtures thereof; most preferred is ethanol.

The level of mono- and di- hydric $C_1$–$C_{12}$ alcohols, especially the $C_1$–$C_6$ alcohols, in the present compositions should generally be no more than about 50%, by weight of the composition, preferably no more than about 35%, more preferably no more than about 30%, even more preferably no more than about 25%, and most preferably from 0% to no more than about 15%.

Optional polar solvents useful in the present invention also include, for example, propylene carbonate and 3-methyl-2-oxazolidinone.

Hydrogel Forming Polymeric Gelling Agent

The compositions will comprise aqueous gel formed from a highly absorbent hydrogel forming polymeric gelling agent. The compositions will contain from about 0.001% to about 5%, by weight of the composition, preferably from about 0.01% to about 5%, more preferably from about 0.05% to about 1%, most preferably from about 0.1% to about 0.75% of such hydrogel forming polymeric gelling agent, calculated based on the dry weight of the hydrogel forming polymeric gelling agent.

The hydrogel forming polymeric gelling agent hereof is highly absorbent of water, and will generally be able to absorb at least about 40 g water (deionized) per gram of gelling agent, preferably at least about 60 g/g, more preferably at least about 80 gig. These values, referred to as "Absorptive Capacity" herein can be determined according to the procedure in the Absorptive Capacity "Tea Bag" test in the Experimental Section below.

The hydrogel forming polymeric gelling agent hereof will also preferably be characterized by an extractable polymer content (e) of no more than about 20%, more preferably no more than about 12%, most preferably no more than about 10%. The extractable polymer content (e) is determined according to the procedures set forth in the Experimental Section, below.

The hydrogel forming polymeric material, when in dry form, will generally be in the form of particles or fibers. Particles will preferably have a weight average particle size (diameter, or equivalent diameter in the case of non-spherical particles) of from about 5 to about 500 microns, preferably from about 10 to about 60 microns, more preferably from about 10 to about 50 microns. Fibrous hydrogel forming polymeric gelling agent preferably have diameters (or equivalent diameters in the case of non-round fibers) of from about 5 to about 100 microns, preferably from about 15 to about 50 microns, and lengths of from about 0.1 mm to about 5 mm more preferably from about 0.5 mm to about 2 mm. It is contemplated that larger or smaller particles or fibers can be used, although they are not preferred, as larger particles or fibers may provide a grainier or a more string-like product feel, and smaller particles may result in processing difficulties. If relatively large particles or fibers are used during manufacture, improved finished product aesthetics can be obtained by sheer mixing the compositions or other mixing operations during processing of the compositions.

In general, the hydrogel forming polymeric gelling agent materials of the present invention are at least partially crosslinked polymers prepared from polymerizable, unsaturated acid-containing monomers which are water-soluble or become water-soluble upon hydrolysis. These include monoethylenically unsaturated compounds having at least one hydrophilic radical, including olefinically unsaturated acids and anhydrides which contain at least one carbon-carbon olefinic double bond.

With respect to these monomers, water-soluble means that the monomer is soluble in deionized water at 25° C. at a level of at least 0.2%, preferably at least 1.0%.

Upon polymerization, monomeric units as described above will constitute from about 25 mole percent to 99.99 mole percent, more preferably from about 50 mole percent to 99.99 mole percent, most preferably at least about 75 mole percent of the polymeric gelling agent material (dry polymer weight basis). Two or more different monomer types of the previously described acid group-containing monomers may be copolymerized in order to provide the hydrogel-forming polymeric gelling material. Exemplary types of such acid groups and other hydrophilic groups include carboxyl, carboxylic acid anhydride, carboxylic salt, sulfonic acid, sulfonic acid salt, hydroxyl, ether, amide, amino and ammonium salt groups.

Hydrogel forming polymeric gelling agents suitable for use herein are well known in the art, and are described, for example, in U.S. Pat. No. 4,076,663, Masuda et al., issued Feb. 28, 1978; U.S. Pat. No. 4,062,817, Westerman, issued Dec. 13, 1977; U.S. Pat. No. 4,286,082, Tsubakimoto et al., issued Aug. 25, 1981; U.S. Pat. No. 5,061,259, Goldman et al., issued Oct. 29, 1991, and U.S. Pat. No. 4,654,039, Brandt et al., issued Mar. 31, 1987 all of which are incorporated herein in their entirety.

Hydrogel forming polymeric gelling agents suitable for use herein are also described in U.S. Pat. No. 4,731,067, Le-Khac, issued Mar. 15, 1988, U.S. Pat. No. 4,743,244, Le-Khac, issued May 10, 1988, U.S. Pat. No. 4,813,945, Le-Khac, issued Mar. 21, 1989, U.S. Pat. No. 4,880,868, Le-Khac, issued Nov. 14, 1989, U.S. Pat. No. 4,892,533, Le-Khac, issued Jan. 9, 1990, U.S. Pat. No. 5,026,784, Le-Khac, issued Jun. 25, 1991, U.S. Pat. No. 5,079,306, Le-Khac, issued Jan. 7, 1992, U.S. Pat. No. 5,151,465, Le-Khac, issued Sep. 29, 1992, U.S. Pat No. 4,861,539, Allen, Farrer, and Flesher, issued Aug. 29, 1989, U.S. Pat. No. 4,962,172, Allen, Farrer, and Flesher, issued Oct. 9, 1990, all incorporated herein by reference in their entireties.

Examples of suitable water-soluble monomers from which monomer units of the polymers hereof can be derived are as follows:

1. Carboxyl group-containing monomers (carboxylic acid-containing): monoethylenically unsaturated mono or poly-carboxylic acids, such as (meth) acrylic acid (meaning acrylic acid or methacrylic acid; similar notations are used hereinafter), maleic acid, fumaric acid, sorbic acid, iraconic acid, citraconic acid, tricarboxy ethylene, and ethacrylic acid;

2. Carboxylic acid anhydride group-containing monomers: monoethylenically unsaturated polycarboxylic acid anhydrides, such as maleic anhydride;

3. Carboxylic acid salt-containing monomers: water-soluble salts (alkali metal salts, ammonium salts, amine salts, etc.) of monoethylenically unsaturated mono- or poly-carboxylic acids [such as sodium (meth)acrylate, trimethylamine (meth)acrylate, triethanolamine (meth) acrylate, sodium maleate, methylamine maleate];

4. Sulfonic acid group-containing monomers: aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth) acrylate, 2-hydroxy-3-(meth)acryloxy propyl sulfonic acid, 2-acylamido-2-methyl propane sulfonic acid];

5. Sulfonic acid salt group-containing monomers: alkali metal salts, ammonium salts, amine salts of sulfonic acid group-containing monomers as mentioned above.

6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxyethyl (meth)acrylate, hydroxypropyl (meth)acrylate, triethylene glycol (meth)acrylate, poly(oxyethylene oxypropylene) glycol mono (meth)allyl ether (in which hydroxyl groups may be etherified or esterified).

7. Amide group-containing monomers: (meth) acrylamide, N-alkyl (meth)acrylamides (such as N-methylacrylamide, N-hexylacrylamide), N,N-dialkyl (meth)acryl amides (such as N,N-dimethylacrylamide, N,N'-di-n-propylacrylamide), N-hydroxyalkyl (meth)acrylamides [such as N-methylol(meth)acrylamide, N-hydroxyethyl (meth)acrylamide], N,N-dihydroxyalkyl (meth)acrylamides [such as N,N-dihydroxyethyl (meth)acrylamide], vinyl lactams (such as N-vinylpyrrolidone);

8. Amino group-containing monomers: amino group-containing esters (e.g. dialkylaminoalkyl esters, dihydroxyalkylaminoalkyl esters, morpholinoalkyl esters, etc.) of monoethylenically unsaturated mono- or di-carboxylic acid [such as dimethlaminoethyl (meth)acrylate, diethylaminoethyl (meth)acrylate, morpholinoethyl (meth)acrylate, dimethyl aminoethyl fumarate], heterocyclic vinyl compounds [such as vinyl pyridines (e.g. 2-vinyl pyridine, 4-vinyl pyridine, N-vinyl pyridine), N-vinyl imidazol]; and 9. Quaternary ammonium salt group-containing monomers: N,N,N-trialkyl-N-(meth)acryloyloxyalkylammonium salts [such as N,N,N-trimethyl-N-(meth)acryloyloxyethylammonium chloride, N,N,N-triethyl-N(meth)acryloyloxyethylammonium chloride, 2-hydroxy-3-(meth)acryloyloxypropyl trimethyl ammonium chloride], and monomers as mentioned in British patent specification No. 1,034,296.

Suitable monomers which become water-soluble by hydrolysis, for use in this invention instead of or in conjunction with the water-soluble monomers, include monethylenically unsaturated compounds having at least one hydrolyzable group, such as ester and nitrile groups. Such monomers having an ester group include for example, lower alkyl (C1–C3) esters of monoethylenically unsaturated carboxylic acids, such as methyl (meth)acrylate, ethyl (meth)acrylate and 2-ethylhexyl (meth)acrylate; and esters of monoethylenically unsaturated alcohols [vinyl esters, (meth)-allyl ester, etc.], such as vinyl acetate and (meth) allyl acetate. Suitable nitrile group-containing monomers include (meth) acrylonitrile.

Preferred monomers include carboxylic acid monomers, or anhydrides or salts thereof. Especially preferred monomers include acrylic acid, methacrylic acid, and maleic acid, and anhydrides and salts thereof. Acrylic acid and combinations of acrylic acid and acrylate salt (e.g. sodium acrylate) are particularly preferred.

While at least 25 mole percent (preferably at least about 35%, more preferably at least about 50%) of the hydrogel-forming polymer compositions herein should be prepared from acid group-containing monomers, some non-acid monomers may also be used to prepare the hydrogel-forming polymer compositions herein (prior to neutralization). It is particularly useful to incorporate non-acid monomers into polymers to be formed into fibers, in order to increase the flexibility of the final polymeric material. Such non-acid monomers can include, for example, the water-soluble or water-dispersible esters of the foregoing acid-containing monomers as well as monomers which contain no carboxyl or sulfonic acid groups at all. Optional non-acid monomers can thus include, for example, carboxylic acid or sulfonic acid ester-containing monomers e.g. $C_1$–$C_4$ esters, hydroxyl group-containing monomers, amide group-containing monomers, amino group-containing monomers, nitrile group containing monomers, quaternary ammonium salt group-containing monomers and unsaturated polymerzable hydrocarbons, such as alph-olefins, vinyl monomers, and vinylidene monomers. Examples include ethylene, propylene, isobutylene, 1-butylene, vinyl acetate, methyl vinyl ether, isobutyl vinyl ether, and styrene compounds of the formula:

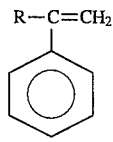

wherein R represents H or a $C_1$–$C_6$ alkyl, and wherein the benzene ring may be substituted with low molecular weight alkyls (e.g. $C_1$–$C_4$) or hydroxy groups. These non-acid monomers are well known materials and are described in greater detail, for example, in Masuda et al., U.S. Pat. No. 4,076,663, issued Feb. 28, 1978; and in Westerman, U.S. Pat. No. 4,062,817, issued Dec. 13, 1977; and U.S. Pat. No. 5,151,465 Le-Khac, issued Sep. 29, 1992; each of which are already incorporated herein by reference. If present at all, such non-acid monomers should generally be used only to such an extent that, prior to neutralization, no more than 75% mole percent of the polymer compositions herein are prepared from such non-acid monomers, preferably no more than about 65%, more preferably no more than about 50%.

Especially preferred are copolymers of maleic acid, maleic anhydride, or malic acid salt with isobutylene or other $C_3$–$C_6$, preferably $C_4$, vinyl monomers most preferably isobutylene at a mole precent of from about 35% to about 65% maleic monomer units to about 65% to about 35% isobutylene or other $C_3$–$C_6$ vinyl monomers.

In the hydrogel-forming polymeric gelling agent the polymeric component formed from unsaturated, acid-containing monomers may be grafted on to other types of polymer moieties such as starch or cellulose.

Suitable starches include, for example, natural starches such as sweet potato starch, potato starch, wheat starch, corn starch, rice starch, tapioca starch, and the like, and processed or modified starches such as alpha-starch, dextrine, oxidized starch, dialdehyde starch, alkyl-etherified starch, allyl-etherified starch, oxyalkylated starch, aminoethyl-etherified starch, cyanoethyl-etherified starch and the like.

Suitable celluloses include, for example, celluloses obtained from wood, leaves, stems, bast, seed fluffs, and the like; and modified celluloses such as alkyl-etherified cellulose, organic-acid-esterified cellulose, oxidized cellulose, hydrocellulose, and the like. Starch grafted materials of this type are especially preferred for use herein.

Whatever the nature of the monomer components of the hydrogel-forming polymeric gelling agents used in the present compositions, the polymers thereof will be crosslinked. Suitable cross-linking agents are well know in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages.

Cross-linking agents having at least two polymerizable double bonds include (i) di- or polyvinyl compounds such as divinylbenzene and divinyltoluene; (ii) di- or poly-esters of unsaturated mono- or polycarboxylic acids with polyols including, for example, di- or triacrylic acid esters of polyols such as ethylene glycol, trimethylol propane, glycerine, or polyoxyethylene glycols; (iii) bisacrylamides such as N,N-methylenebisacrylamide; (iv) carbamyl esters that can be obtained by reacting polyisocyanates with hydroxyl group-containing monomers; (v) di- or poly-allyl ethers of polyols; (vi) di- or poly-allyl esters of polycarboxylic acids such as diallyl phthalate, diallyl adipate, and the like; (vii) esters of unsaturated mono- or poly-carboxylic acids with mono-allyl esters of polyols such as acrylic acid ester of polyethylene glycol monoallyl ether; and (viii) di-or tri-allyl amine.

Cross-linking agents having at least one polymerizable double bond and at least one functional group reactive with the acid-containing monomer material include N-methylol acrylamide, glycidyl acrylate, and the like. Suitable cross-linking agents having at least two functional groups reactive with the acid-containing monomer material include glyoxal; polyols such as ethylene glycol and glycerol; polyamines such as alkylene diamines (e.g., ethylene diamine), poly-alkylene polyamines, polyepoxides, di- or polyglycidyl ethers and the like. Suitable polyvalent metal cross-linking agents which can form ionic cross-linkages include oxides, hydroxides and weak acid salts (e.g., carbonate, acetate and the like) of alkaline earth metals (e.g., calcium, magnesium) and zinc, including, for example, calcium oxide and zinc diacetate.

Cross-linking agents of many of the foregoing types are described in greater detail in Masuda et al., U.S. Pat. No. 4,076,663, issued Feb. 28, 1978, and Allen et al., U.S. Pat. No. 4,861,539, issued Aug. 29, 1989, both incorporated herein by reference. Preferred cross-linking agents include the di- or polyesters of unsaturated mono- or polycarboxylic acids mono-allyl esters of polyols, the bisacrylamides, and the di- or tri-allyl amines. Specific examples of expecially preferred cross-linking agents include N,N'-methylenebisacrylamide and trimethylol propane triacrylate.

The cross-linking agent will generally constitute from about 0.001 mole percent to 5 mole percent of the resulting hydrogel-forming polymeric material. More generally, the cross-linking agent will constitute from about 0.01 mole percent to 3 mole percent of the hydrogel-forming polymeric gelling agent used herein.

The hydrogel forming polymeric gelling agent herein is at least partially crosslinked, however the degree of crosslinking must be high enough such that the resulting polymer does not exhibit a glass transition temperature (Tg) below about 140° C., and accordingly, the term "hydrogel forming polymeric gelling agent," as used herein, shall mean polymers meeting this parameter. Preferably the hydrogel forming polymeric gelling agent does not have a Tg below about 180° C., and more preferably does not have a Tg prior to decomposition of the polymer, at temperatures of about 300° C. or higher. The Tg can be determined by differential scanning calorimetry (DSC) conducted at a cooling rate of 20.0° C./minute with 5 mg or smaller samples. The Tg is calculated as the midpoint between the onset and endset of heat flow change corresponding to the glass transition on the DSC heat capacity cooling curve. The use of DSC to determine Tg is well known in the art, and is described by B. Cassel and M. P. DiVito in "Use of DSC To Obtain Accurate Thermodynamic and Kinetic Data", American Laboratory, January 1994, pp 14–19, and by B. Wunderlich in *Thermal Analysis*, Academic Press, Inc., 1990.

The hydrogel forming polymeric gelling hereof are preferably employed in their partially neutralized form. For purposes of this invention, such materials are considered partially neutralized when at least 25 mole percent, and preferably at least 50 mole percent of monomers used to form the polymer are acid group-containing monomers which have been neutralized with a base. Suitable neutralizing bases cations include hydroxides of alkali and alkaline earth metal (e.g. KOH, NaOH), ammonium, substituted ammonium, and amines such as amino alcohols (e.g., 2-amino-2-methyl-1,3-propanediol, diethanolamine, and 2-amino-2-methyl-1-propanol. This percentage of the total monomers utilized which are neutralized acid group-containing monomers is referred to herein as the "degree of neutralization." The degree of neutralization will preferably not exceed 98%.

Hydrogel forming polymer gelling agent materials can be prepared by reacting monomers and cross-linking agents, as described above, in conventional manners. Prior art hydrogel forming polymeric gelling agent synthesis procedures are well known in the art and are also disclosed, for example, in the previously referenced U.S. Pat. Nos. 4,654,039, 4,286,082, and 4,340,706.

Suitable hydrogel forming polymeric gelling agents in the form of particles are commercially available from Hoechst Celanese Corporation, Portsmouth, Va., USA (Sanwet™ Superabsorbent Polymers) Nippon Shokubai, Japan (Aqualic™, e.g., L-75, L-76) and Dow Chemical Company, Midland, Mich., USA (Dry TeCh™).

Suitable hydrogel forming polymeric gelling agents in the form of fibers are commercially available from Camelot Technologies Inc., Leominstr, Mass., USA (Fibersorb™, e.g., SA 7200H, SA 7200M, SA 7000L, SA 7000, and SA 7300).

Water

The compositions of the present invention will comprise at least about 25%, by weight, water, preferably from about 25% to about 85%, more preferably from about 30% to about 75%, most preferably from about 40% to about 60%.

The water content includes water incorporated into the hydrogel formed from the polymeric gelling agent as well as other free (not complexed) water in the composition, including that intermixed with the polyhydroxy solvent (as defined above), other polar solvent, or other ingredients of the composition.

Compositions

The compositions can be provided in a variety of product rheologies, including both soft and hard gels. However the preferred compositions will be hard gels having a Penetration Value of at least about 60 (measured in tenths of a millimeter), preferably from about 65–200, more preferably from about 70 to about 160, most preferably from about 75 to about 120. Penetration Value is determined according to the standard procedure set forth by ASTM Method D-5 for gel stick compositions stored prior to testing at about 26.7° C. (80° F.) for at least 24 hours, using an automatic fixed time penetrometer (e.g. Fisher Scientific Co., Model 13-399-10 or equivalent) and a taper-tipped penetration needle as specified in ASTM Method D 1321-DIN 51 579. The total weight of the needle and shaft in the penetrometer is 50.00±0.05 grams.

Optional Ingredients

A wide variety of optional ingredients can be incorporated into the present compositions. These include components for improving cosmetics, efficacy, stability, and aesthetics. Such optional ingredients include: emollients; humectants; soothing agents; dyes and pigments; medicaments; pH buffering agents; fillers; and the like.

Buffering agents include coconut monoethanolamide, sodium hydroxide, stearamide, monoethanolamide, acetamide MEA, zinc acetate, sodium chloride, potassium chloride, zinc stearate, aluminum oxide, calcium acetate, zinc oxide, magnesium oxide, calcium carbonate, calcium hydroxide, sodium carbonate, magnesium carbonate, zinc carbonate, calcium oxide, and mixtures thereof.

Fillers include silicate powders such as talc, aluminum silicate, magnesium silicate, metallic stearates, polyethylene, colloidal silica, clays such as bentonite, and particulate hydrophilic polymers such as cellulose ether polymers, modified starches, polyamides, and polypeptides.

Soothing agents are ingredients that can mitigate irritation to the skin caused by other ingredients or pre-existing conditions (e.g. burns, abrasions, cuts etc.). Exemplary soothing agents include aloe vera, allantoin, avocado oil and other vegetative oils, and lichen extract.

Method of Manufacture

The compositions of the present invention may be made by any of the typical methods known in the art for formulating deodorant gel compositions, as modified below to incorporate the polymeric hydrogel component. As will be apparent to those skilled in the art, the particular method will be dependent upon the selection of the nonpolymeric gelling agent.

In general, the compositions can be made as follows: Prepare a premix A of the hydrogel forming polymeric gelling agent and water and then mix to form a homogenous gel. Optionally shear mix to reduce gel particle size and improve smoothness to the touch. Prepare a premix B with the soap gelling agent, and the polyhydroxy solvent for the soap gelling agent, with mixing at a temperature high enough to dissolve the soap gelling agent (typically about 70°–95° C.). Combine premixes A and B with mixing and preferably cool to about 60°–80° C. if additional volatile ingredients are to be added. Add other ingredients, as may be applicable, to either premix or to the final mixture prior to cooling.

Method For Use

The present invention provides methods for controlling malodor. These methods comprise applying to the skin of a human a safe and effective amount of the gel deodorant composition of the present invention. The term "a safe and effective amount" as used herein, is an amount which is effective in eliminating or substantially reducing malodor associated with human underarm perspiration while being safe for human use at a reasonable risk/benefit ratio. Typically, the safe and effective amount used is from about 0.1 gram per axilla to about 2.0 gram per axilla.

EXPERIMENTAL

A) Absorptive Capacity "Tea Bag" Test

Absorptive Capacity can be determined by a gravimetric analytical technique using deionized water as the fluid for which Absorptive Capacity of the polymeric gelling agent is to be calculated. A sample of polymeric gelling agent is placed within a tea bag, immersed in an excess of deionized water for a specified period of time, and then centrifuged for a specific period of time. The ratio of polymeric gelling agent final weight after centrifuging minus initial weight (net fluid gain) to initial weight determines the Absorptive Capacity.

The following procedure is conducted under standard laboratory conditions at 23° C. (73° F.) and 50% relative humidity. Using a 6 cm×23 cm cutting die, the tea bag material is cut, folded in half lengthwise and sealed along two sides with a T-bar sealer to produce a 6 cm×6 cm tea bag square. The tea bag material utilized is a grade 1234 heat sealable material, obtainable from C. H. Dexter, Division of the Dexter Corp.,Windsor Locks) Connecticut, U.S.A., or equivalent. Lower porosity tea bag material should be used if required to retain fine particles or fibers of polymeric gelling agent. 0.200 grams plus or minus 0.005 grams of the polymeric gelling agent is weighed onto a weighing paper and transferred into the tea bag and the top (open end) of the tea bag is sealed. An empty tea bag is sealed at the top and is used as a blank. Approximately 300 milliliters of deionized water are poured into a 1,000 milliliter beaker. The blank tea bag is submerged in the deionized water. The tea bag containing the polymeric gelling agent (the sample tea bag) is held horizontally to distribute the material evenly throughout the tea bag. The tea bag is laid on the surface of the deionized water. The tea bag is allowed to wet, for a period of no more than one minute, and then is fully submerged and soaked for 60 minutes. Approximately 2 minutes after the first sample is submerged, a second set of tea bags, prepared identically to the first set of blank and sample tea bags, is submerged and soaked for 60 minutes in the same manner as the first set. After the prescribed soak time has elapsed, for each set of tea bag samples, the tea bags are promptly removed (using tongs) from the deionized water. The samples are then centrifuged as described below. The centrifuge used is a Delux Dynac II Centrifuge, Fisher Model No. 05-100-26, obtainable from the Fisher Scientific Co. of Pittsburgh, Pa., or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, a 7.935 inch (20.155 cm) inside diameter, and 9 rows each of approximately 106 3/32 inch (0–238 cm) diameter circular holes equally spaced around the circumference of the outer wall, and having a basket floor with six ¼ inch (0.635 cm) diameter circular drainage holes equally spaced around the circumference of the basket floor at a distance of ½ inch (1.27 cm) from the interior surface of the outer wall to the center of the drainage holes, or an equivalent. The basket is mounted in the centrifuge so as to rotate, as well as brake, in unison with the centrifuge. The-sample tea bags are positioned in the centrifuge basket with a folded end of the tea bag in the direction of the centrifuge spin to absorb the initial force. The blank tea bags are placed to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm, a timer is set for 3 minutes. After 3 minutes, the centrifuge is turned off and the brake is applied. The first sample tea bag and the first blank tea bag are removed and weighed separately. The procedure is repeated for the second sample tea bag and the second blank tea bag.

The Absorptive Capacity (AC) for each of the samples is calculated as follows: AC=(sample tea bag weight after centrifuge minus blank tea bag weight after centrifuge minus polymeric gelling agent weight)/(dry polymeric gelling agent). The Absorptive Capacity value for use herein is the average absorptive capacity of the two samples.

B. Extractable Polymer Content Determination

Depending upon the type of hydrogel-forming crosslinked polymeric gelling agent involved, two different methods are used herein to calculate extractable polymer content. For carboxylic acid-based polymeric gelling agent a potentiometric procedure is used to determine extractables. For sulfonic acid-based polymeric gelling agent, a gravimetric procedure is employed. It should be noted that both of these procedures may provide results that include in the total amount of extractable material those extractable components in the polymeric gelling agent which are not polymeric. Therefore, if a given polymer sample is known or believed to contain significant amounts of non-polymeric extractable material, such non-polymeric extractable material should be removed from the analyte in conventional fashion before running the extractable polymer content determination hereinafter described.

(1) Carboxylic Acid-Based Polymeric Gelling Agent

Extractable polymer content of carboxylic acid-based polymeric gelling agent is determined by admixing the polymeric gelling agent with deionized water for a period of time sufficient to substantially approach equilibrium with respect to extraction of polymer material from the hydrogel which is formed. The hydrogel/deionized water mixture is allowed to settle and a portion thereof is filtered. An aliquot of this filtrate is then taken, and the free acid groups on the polymer material dissolved in this filtrate are titrated to pH 10 with base. All of the carboxylate groups are then titrated to pH 2.7 with acid. These titration data are then used to calculate the amount of extractable polymer in the polymeric gelling agent sample.

(a) Preparation of the Extractable Polymer-Containing Filtrate Samples 1. 0.40 to 0.41 g of polymeric gelling agent is accurately (to ±0.1 mg) weighed into a 150 ml disposable beaker. If glass beakers are used they must be acid washed prior to use. (Glassware should be washed three times with dilute HCl [conc. HCl diluted 1:4 with dieionized water], then three times with deionized water. This procedure removes trace of detergents and other contaminants which would otherwise interfere with the titration.)

2. 75 ml of deionized water are added.

3. Samples are slowly stirred for a period of time sufficient to reach equilibrium. Equilibrium is generally reached within 16 hour periods. If extractable polymer content is to be measured as a function of time, then 1, 6, and 16 hour periods are generally sufficient to define the extractables versus time curve.

4. Samples are allowed to settle for 15 minutes.

5. Using a 3 ml disposable syringe and 0.22 micron filters, enough solution is filtered so that a 20 ml aliquot can be taken.

(b) Titration Conditions

1. If the titrations are to be performed manually, great care must be taken to assure that equilibrium is reached after each addition of titrant.

2. A 20 ml aliquot of the filtrate is transferred to a 50 ml disposable beaker. If glass beakers are being used, they must be acid washed prior to use as noted herein before.

3. The aliquot is titrated to pH 10 with 0.1N NaOH.

4. The aliquot is then back titrated to pH 2.7 with 0.1N HCl.

5. Step 3 and 4 are performed on 20 ml of deionized water to obtain titration blinks for both steps of the titration.

(c) Calculations

1. The amount of polymerized acid moleties (e.g., acrylic acid) (in millimoles) in the supernatant aliquot ($M_a$) is given by:

$$M_a = (V_a - V_{ab}) \times N_a \text{ millimoles (mm)}$$

where:

$V_a$=The volume (in ml) of acid required to titrate the aliquot to pH 10;

$V_b$=The volume (in ml) of acid required to titrate 20 ml of deionized water to pH 10; and $N_a$=The normality (in meq/ml) of the acid (nominally 0.10 meq/ml)

2. The total amount of polymerized acid moleties (e.g. acrylic acid) plus polymerized neutralized acid moleties (e.g., sodium acrylate) (in mm) in the supernatant aliquot ($M_t$) is given by:

$$M_t = (V_b - V_{bb}) \times N_b \text{ millimoles}$$

where:

$V_b$=The volume (in ml) of base required to titrate the aliquot from pH 10 down to pH 2.7;

$V_{bb}$=The volume (in ml) of base required to titrate 20 ml of deionized water from pH 10 down to pH 2.7; and $N_b$=The normality (in meq/mi) of the base (nominally 0.10 meq/ml).

3. The amount of polymerized neutralized acid moleties (e.g., sodium acrylate) (in mm) in the original supernatant aliquot ($M_b$) is given by:

$$M_b = M_t - M_a$$

4. The total amounts of polymerized acid moleties ($W_a$) and polymerized neutralized acid moieties ($W_b$) (e.g., acrylic acid plus sodium acrylate) extracted (in mg) are given by:

$$W_a = M_a \times E_a \times D \text{ and}$$

$$W_b = M_b \times E_b \times D$$

where:

$E_a$=The equivalent weight of add moiety in polyacid moiety (e.g., acrylic acid in polyacrylic acid=72 meq/mg).

$E_b$=The equivalent weight of neutralized acid moiety in neutralized polyacid moiety (e.g., sodium acrylate in sodium polyacrylate=94 meq/mg).

D=The dilution factor (75 ml/20 ml=3.75).

5. The percent extractable polymer in the polymeric gelling agent sample (e) is given by:

$$e = ((W_a + W_b) \times 100)/W$$

where: W=The sample weight in mg.

2. Sulfonic Acid-Containing Polymeric Gelling Agent

Extractable polymer content of sulfonic acid-based polymeric gelling agent is determined by a gravimetric procedure wherein hydrogel samples are swollen overnight in deionized water, and the polymer content in the nitrate is gravimetrically determined. The particular procedure of the gravimetric extractables determination are set forth as follows:

Into a 500 ml Erlenmeyer flask is weighed accurately (to +/–0.1 mg) about 0.25 grams of dry polymeric gelling agent ($W_p$). 250 ml of deionized water is added and the mixture is stirred slowly for 1 hour. After this hour has passed, stirring is stopped, and the swollen gel is allowed to settle for about 16 hours. The supernatant is filtered using a 3 ml disposable syringe and 0.22 micron filter to obtain at least 40 ml of filtrate. Exactly 40 ml of filtrate is placed into a clean 100 ml round-bottomed flask, and the solution is concentrated on a rotary evaporator filtrate. Exactly 40 ml of filtrate is placed into a clean 100 ml round-bottomed flask, and the solution is concentrated on a rotary evaporator (water aspirator vacuum, bath temperature 55° C.). The remaining 2–3 ml of solution is transferred quantitatively to a tared weighing vial with the aid of additional deionized water. The solution in the weighing vial is reduced to dryness in an oven at 120° C. The vial is cooled, reweighed, and the weight of residue ($W_r$) is determined using the tare weight of the vial. The percent extractable polymer (e) is calculated from the weight of dry polymer ($W_p$) and weight of residue ($W_r$) by the following equation:

$$e = (W_r \times 250 \times 100)/(W_p \times 40)$$

EXAMPLES

The following examples further describe and demonstrate embodiments within the scope of the present invention. These examples are solely for the purpose of illustration and are not to be construed as limitations of the present invention as many variations are possible without departing from the spirit or scope thereof.

| Ingredient (wt. %) | Example # | | | |
|---|---|---|---|---|
| | 1 | 2 | 3 | 4 |
| Triclosan | 0.300 | 0.080 | 0.080 | 0.300 |
| Dipropylene Glycol | 30.310 | 20.755 | — | 43.905 |
| Propylene Glycol | 13.700 | — | — | 22.205 |
| Water | 28.500 | 50.000 | 75.000 | 25.000 |
| PEG-4[1] | 0.599 | 20.599 | 12.903 | 0.599 |
| PEG-8[2] | 10.000 | — | — | — |
| Glycerine | 8.105 | — | 5.000 | — |
| Hydrogel-Forming Polymeric Gelling Agent | 0.020[3] | 0.100[3] | 0.150[3] | 0.0 |
| Sodium Stearate | 5.000 | 5.000 | 5.300 | 4.500 |
| Sodium Hydroxide Solution (50% solution) | 0.040 | 0.040 | 0.040 | 0.040 |
| Color Solution | 0.001 | 0.001 | 0.001 | 0.001 |
| Tetrasodium EDTA | 0.025 | 0.025 | 0.025 | 0.025 |
| Fragrance | 3.400 | 3.400 | 3.400 | 3.400 |
| | 5 | | 6 | 7 |
| Triclosan | 0.080 | | 0.080 | 0.080 |
| Dipropylene Glycol | 13.695 | | — | — |
| Propylene Glycol | — | | — | — |
| Water | 45.000 | | 60.000 | 50.000 |
| PEG-4[1] | 20.599 | | 20.599 | 21.049 |
| PEG-8[2] | — | | — | — |
| Glycerine | 11.560 | | 10.400 | 20.000 |
| Hydrogel-Forming Polymeric Gelling Agent | 0.100[4] | | 0.250[4] | 0.010[3] |
| Sodium Stearate | 4.700 | | 5.200 | 5.300 |

| Ingredient (wt. %) | Example # | | |
|---|---|---|---|
| Sodium Hydroxide Solution (50% solution) | 0.040 | 0.040 | 0.040 |
| Color Solution | 0.001 | 0.001 | 0.001 |
| Tetrasodium EDTA | 0.025 | 0.025 | 0.025 |
| Fragrance | 3.400 | 3.400 | 3.400 |

[1] Carbowax PEG-200 ™ Union Carbide Corporation (Danbury, CT, USA).
[2] Carbowax PEG-400 ™ Union Carbide corporation (Danbury, CT, USA).
[3] Fibrous maleic anhydride/isobutylene crosslinked hydrogel-forming polymeric gelling agent, Fibersorb SA 7200H, from Camelot Technologies, Inc. (Leominster, MA, USA).
[4] Particulate acrylic acid crosslinked hydrogel-forming polymeric gelling agent, Aqualic ™ L-74 from Nippon Shokubai, Japan. Alternatively, add Nalco N-1181 from Nalco Chemical Company (Naperville, IL, USA) can be used.

The above example formulations are made as follows. Seventy to eighty percent of total required water for the formulation is added to a mixing vessel equipped with a rotor stator homogenizer. The hydrogel forming polymeric gelling agent is added, with mixing at 9500 revolutions per minute (rpm), at rate of 3 grams/minute until a clear hydrogel is formed (Premix A). Heat Premix A to 68°–74° C. (155°–165° F.) with stirring. In a separate container equipped with stirring blade, add the remaining water along with the polyhydroxy solvent(s) and other polar solvents as may be applicable, deodorant active (triclosan), and preservative (tetrasodium EDTA). Heat to about 79°–85° C. (175°–185° F.), and stir at 50 rpm (Premix B). Add sodium stearate to Premix B and mix until the solution is clear. Combine Premixes A and B, cool the mixture to 69°–73° C. (157°–163° F.). Add sodium hydroxide solution fragrance and color solution, and mix thoroughly. Pack in a conventional deodorant stick package at about 71° C. (160° F.) and allow to cool to room temperature. The final product will be mild to the skin, efficacious, deodorant gel stick product.

What is claimed is:

1. A deodorant gel composition, comprising:
   (a) from about 0.001% to about 20%, by weight, of deodorant active fragrance, or combination thereof;
   (b) from about 0.01% to about 15%, by weight, of a soap gelling agent selected from the group consisting of salts of $C_{12}$–$C_{40}$ fatty acids, and combinations thereof;
   (c) a hydrogel component comprising from about 0.001% to about 5%, by weight of the composition, of hydrogel forming crosslinked polymeric gelling agent, said hydrogel forming polymeric gelling agent being present in said composition as a gel;
   (d) from about 5% to about 70%, by weight, of a polyhydroxy solvent for said soap gelling agent, said polyhydroxy solvent being selected from the group consisting of: alkyl alcohols having at least three hydroxy groups; polymers of $C_3$–$C_{12}$ alcohols having at least three hydroxy groups per monomer wherein the polymers have a weight average molecular weight of about 800 or less; polyoxyethylenes, polyoxypropylenes, and polyoxyethylene/polyoxypropylene copolymers, having a weight average molecular weight of from about 200 to about 4,000; copolymers of $C_3$–$C_{12}$ alcohols having at least three hydroxy groups with $C_2$–$C_{10}$ dihydric alcohols, said copolymers having a weight average molecular weight of from about 200 to about 4,000; and combinations thereof; and
   (e) at least about 25%, by weight, water, said compositions having a penetration value of from about 60 to about 200 tenths of a millimeter.

2. A deodorant gel composition as in claim 1, wherein said hydrogel forming crosslinked polymeric gelling agent is characterized by not having a Tg below about 180° C.

3. A deodorant gel composition as in claim 2, wherein said composition comprises from about 0.01% to about 5%, by weight, of said hydrogel forming crosslinked polymeric gelling agent, from about 0.5% to about 10%, by weight, of said soap gelling agent, from about 10% to about 60%, by weight, of said polyhydroxy solvent for said soap gelling agent, from about 30% to about 75%, by weight, water, and no more than about 35%, by weight, of mono- and dihydric $C_1$–$C_{12}$ alcohols.

4. A deodorant gel composition as in claim 3, wherein said composition comprises from about 0.05% to about 1%, by weight, of said hydrogel forming crosslinked polymeric gelling agent, from about 1% to about 5%, by weight, of said soap gelling agent, from about 15% to about 50%, by weight, of said polyhydroxy solvent for said soap gelling agent, from about 40% to about 60%, by weight, water and no more than about 30%, by weight, of mono- and dihydric $C_1$–$C_{12}$ alcohol.

5. A deodorant gel composition as in claim 2 wherein said hydrogel forming polymeric gelling agent comprises from about 25 mole % to about 99.99 mole % acid-containing monomer units selected from the group consisting of carboxylic acid-containing monomer units, and salts and anhydrides thereof, and from 0 mole % to about 75 mole %, non-acid monomer units.

6. A deodorant gel composition as in claim 5, wherein said hydrogel forming polymeric gelling agent are derived from the group consisting of acrylic acid, methacrylic acid, maleic acid, fumaric acid, sorbic acid, iraconic acid, citraconic acid, ethacrylic acid, and tricarboxy ethylene, and salts and anhydrides thereof.

7. A deodorant gel composition as in claim 6, wherein said hydrogel forming polymeric gelling agent comprises monomer units derived from acrylic acid, maleic acid, or salts or anhydrides thereof.

8. A deodorant gel composition as in claim 5, wherein said hydrogel forming polymeric gelling agent comprises monomer units derived from about 50 mole % to about 99.99 mole % acrylic acid or salts thereof.

9. A deodorant gel composition as in claim 5, wherein said hydrogel forming polymeric gelling agent is a copolymer of maleic acid or salts or anhydrides thereof, and $C_4$ vinyl monomer.

10. A deodorant gel composition as in claim 9 wherein said copolymer comprises monomer units of from about 35 mole % to about 65 mole % of maleic acid, or salts or anhydrides thereof, and from about 65 mole % to about 35 mole % isobutylene.

11. A deodorant gel composition as in claim 1, wherein said solvent for said soap gelling agent is selected from the group consisting of PEG having an average degree of ethoxylation of from about 4 to about 22, PEG/PPG copolymers having a degree of ethoxylation of from about 4 to about 22 and a ratio of average (ethoxylation) to (ethoxylation plus propoxylation) of less than about 0.5, glycerol, and polyglycerol, and alkyl ethers thereof.

12. A deodorant gel composition as in claim 11 wherein said average degree of ethoxylation for PEG and PEG/PPG copolymers is from about 4 to about 10.

13. A deodorant gel composition as in claim 12, wherein said polyhydroxy solvent comprises a combination of (i) said PEG, PEG/PPG copolymer, or a combination thereof, with (ii) glycerol, polyglycerol, or a combination thereof, at a weight ratio of (i):(ii) of from about 1:5 to about 5:1.

14. A deodorant gel composition as in claim 13, wherein said weight ratio (i):(ii) is from about 3:1 to about 1:3.

15. A deodorant gel composition as in claim 1, wherein said soap gelling agent is selected from the group consisting of salts of $C_{16}$–$C_{22}$ fatty acids.

16. A deodorant gel composition as in claim 15, wherein said soap gelling agent is selected from the group consisting of sodium and potassium salts of myristic acid, palmitic acid, stearic acid, oleic acid, linoleic acid, linolenic acid, and margaric acid.

17. A deodorant gel composition as in claim 16, wherein said soap gelling agent is sodium or potassium stearate, or a combination thereof.

18. A deodorant gel composition as in claim 2, wherein said hydrogel forming polymeric gelling agent is fibrous.

19. A deodorant gel composition as in claim 9, wherein said hydrogel forming polymeric gelling agent is fibrous.

20. A deodorant gel composition as in claim 1, comprising a fragrance.

21. A deodorant gel composition as in claim 1, comprising a deodorant active material.

22. A deodorant gel composition, comprising:

(a) from about 0.001% to about 20%, by weight, of deodorant active fragrance, or combination thereof;

(b) from about 0.01% to about 15%, by weight, of a soap gelling agent selected from the group consisting of salts of $C_{12}$–$C_{40}$ fatty acids, and combinations thereof;

(c) a hydrogel component comprising from about 0.001% to about 5%, by weight of the composition, of hydrogel forming crosslimked polymeric gelling agent, said hydrogel forming polymeric gelling agent being present in said composition as a gel;

(d) from about 5% to about 70%, by weight, of a polyhydroxy solvent for said soap gelling agent, said polyhydroxy solvent being selected from the group consisting of: polymers of $C_3$–$C_{12}$ alcohols having at least three hydroxy groups per wherein the polymers have a weight average molecular weight of about 800 or less; polyoxyethylenes, polyoxypropylenes, and polyoxyethylene/polyoxypropylene copolymers, having a weight average molecular weight of from about 200 to about 4,000; copolymers of $C_3$–$C_{12}$ alcohols having at least three hydroxy groups with $C_2$–$C_{10}$ dihydric alcohols, said copolymers having a weight average molecular weight of from about 200 to about 4,000; and combinations thereof; and (e) at least about 25%, by weight, water said compositions having a penetration value of from about 60 to about 200 tenths of a millimeter.

* * * * *